(12) United States Patent
Iwase et al.

(10) Patent No.: US 10,098,537 B2
(45) Date of Patent: Oct. 16, 2018

(54) IMAGE PROCESSING APPARATUS IMAGE PROCESSING METHOD AND PROGRAM

(71) Applicant: CANON KABUSHIKI KAISHA, Tokyo (JP)

(72) Inventors: Yoshihiko Iwase, Yokohama (JP); Akihiro Katayama, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/181,625

(22) Filed: Jun. 14, 2016

(65) Prior Publication Data

US 2017/0127936 A1     May 11, 2017

Related U.S. Application Data

(63) Continuation of application No. 14/856,108, filed on Sep. 16, 2015, now Pat. No. 9,380,935, which is a (Continued)

(30) Foreign Application Priority Data

Jun. 8, 2010   (JP) ................................. 2010-131257

(51) Int. Cl.
*G06K 9/00* (2006.01)
*A61B 3/10* (2006.01)
(Continued)

(52) U.S. Cl.
CPC ............ *A61B 3/102* (2013.01); *A61B 3/0025* (2013.01); *A61B 3/1225* (2013.01); *A61B 3/1233* (2013.01); *G06K 9/0061* (2013.01); *G06K 9/00604* (2013.01); *G06K 9/6215* (2013.01); *G06T 5/50* (2013.01); *G06T 7/0012* (2013.01);
(Continued)

(58) Field of Classification Search
USPC ................ 382/100, 103, 106–107, 117–118, 382/128–134, 162, 168, 173, 181, 194, 382/209, 219, 232, 254, 258, 274, 276, 382/291, 305, 319, 321, 324; 356/497; 351/206, 246; 345/419
See application file for complete search history.

(56) References Cited

U.S. PATENT DOCUMENTS 7,744,221 B2 *   6/2010   Wei .................... A61B 3/102
                                                                351/200
8,045,176 B2 *  10/2011   Everett ................ A61B 5/0059
                                                                356/497
(Continued)

OTHER PUBLICATIONS

Zawadzki, R., et al "Ultrahigh-resolution optical coherence tomography with monochromatic and chromatic aberration correction", Optics Express, May 26, 2008, pp. 8126-8143, vol. 16, No. 11.
(Continued)

*Primary Examiner* — Seyed Azarian
(74) *Attorney, Agent, or Firm* — Canon USA Inc., IP Division

(57) ABSTRACT

An image processing apparatus includes a calculation unit configured to calculate information indicating similarity among a plurality of tomographic images, and a generation unit configured to generate a tomographic image from the plurality of tomographic images based on the calculated information indicating similarity.

32 Claims, 8 Drawing Sheets

Related U.S. Application Data continuation of application No. 14/580,652, filed on Dec. 23, 2014, now Pat. No. 9,171,367, which is a continuation of application No. 13/702,705, filed as application No. PCT/JP2011/002995 on May 30, 2011, now Pat. No. 8,983,164.

(51) Int. Cl.

| | | |
|---|---|---|
| *G06T 7/00* | (2017.01) | |
| *A61B 3/12* | (2006.01) | |
| *A61B 3/00* | (2006.01) | |
| *G06T 7/32* | (2017.01) | |
| *G06K 9/62* | (2006.01) | |
| *G06T 5/50* | (2006.01) | |
| *A61B 3/14* | (2006.01) | |

(52) U.S. Cl.
CPC .............. *G06T 7/0014* (2013.01); *G06T 7/32* (2017.01); *G06T 7/97* (2017.01); *G06T 2207/10016* (2013.01); *G06T 2207/10072* (2013.01); *G06T 2207/10101* (2013.01); *G06T 2207/20216* (2013.01); *G06T 2207/30041* (2013.01)

(56) References Cited

U.S. PATENT DOCUMENTS

| | | | | |
|---|---|---|---|---|
| 2010/0189366 A1* | 7/2010 | Iizuka | ................... | G06F 17/271 382/209 |
| 2010/0278402 A1* | 11/2010 | Everett | ................ | A61B 5/0059 382/128 |
| 2011/0267340 A1* | 11/2011 | Kraus | ................... | A61B 3/102 345/419 |
| 2011/0299034 A1* | 12/2011 | Walsh | ................... | A61B 3/102 351/206 |
| 2012/0327365 A1* | 12/2012 | Makihira | ............... | A61B 3/113 351/206 |

OTHER PUBLICATIONS

Jorgensen, T.M., et al "Enhancing the signal-to-noise ration in ophthlmic optical coherence tomography by image registration—method and clinical examples", Journal of Biomedical Optics, Jul./Aug. 2007, vol. 12, No. 4.

\* cited by examiner

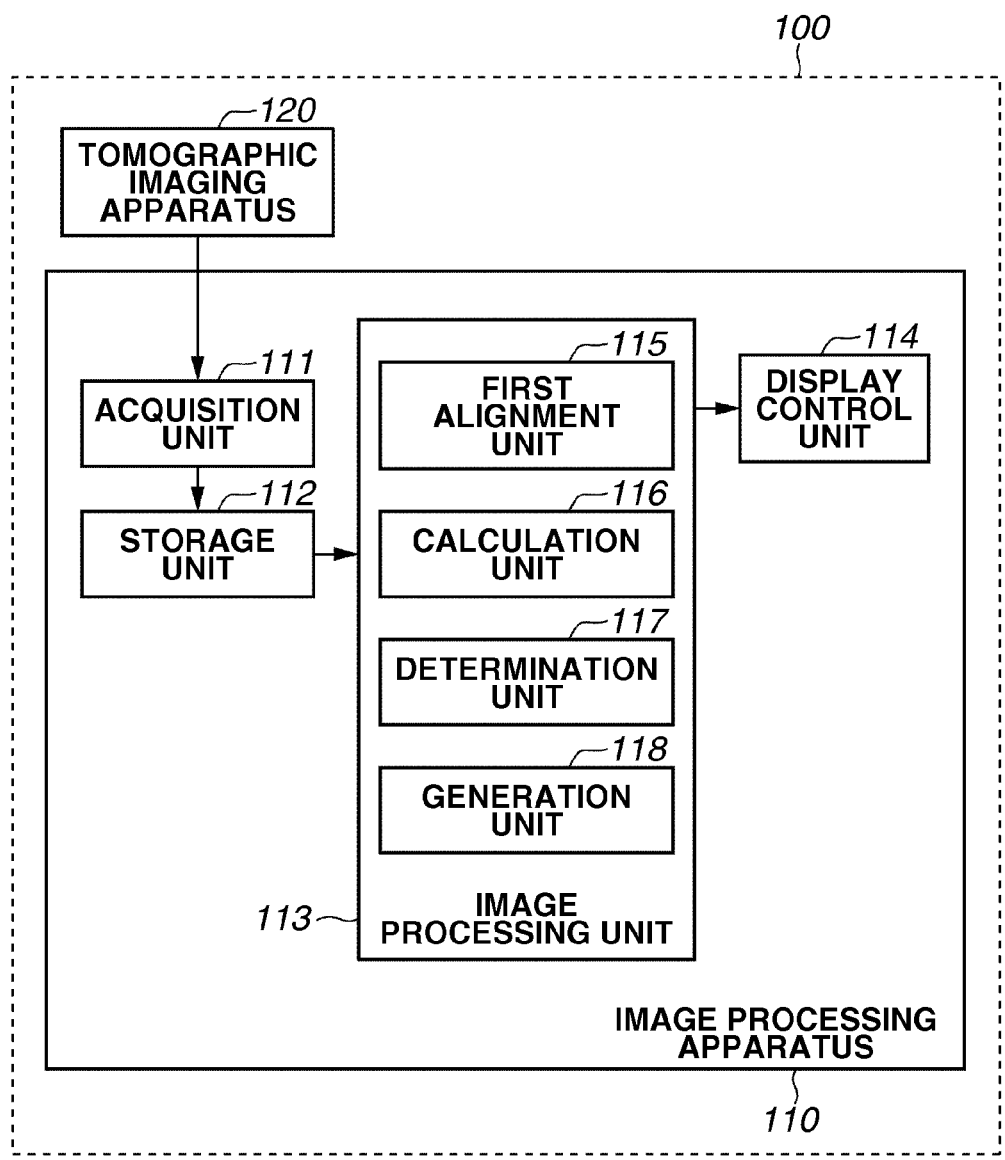

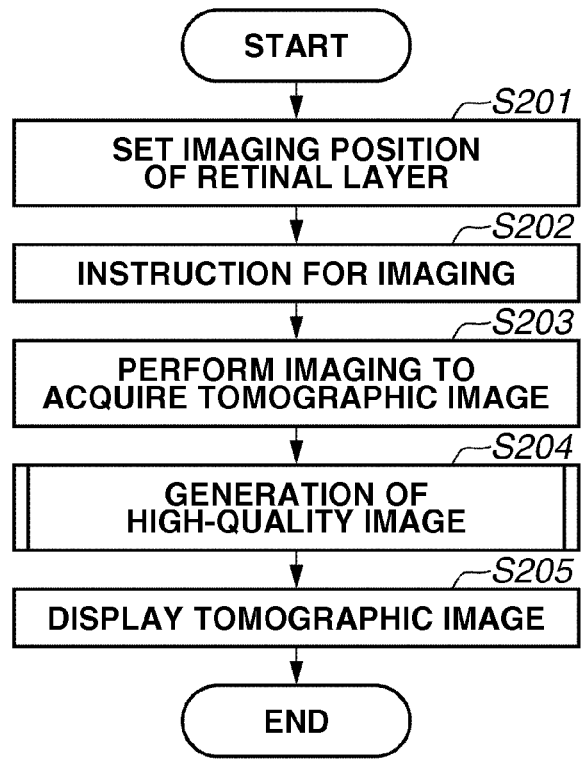
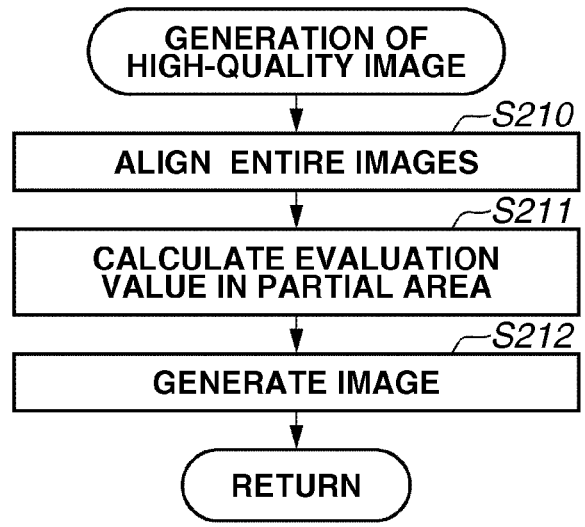

IMAGE PROCESSING APPARATUS IMAGE PROCESSING METHOD AND PROGRAM

CROSS-REFERENCE TO RELATED APPLICATIONS

This application is a Continuation of U.S. patent application Ser. No. 14/856,108, which is a continuation of U.S. application Ser. No. 14/580,652 filed Dec. 23, 2014 (now U.S. Pat. No. 9,171,367), which is a Continuation of U.S. application Ser. No. 13/702,705 (now U.S. Pat. No. 8,983,164), filed Dec. 7, 2012, which is a U.S. national stage application of International Patent Application No. PCT/JP2011/002995, filed May 30, 2011, which claims the priority benefit of Japanese Patent Application No. 2010-131257, filed Jun. 8, 2010. All of the above-named applications are hereby incorporated by reference herein in their entirety.

TECHNICAL FIELD

The present invention relates to a technique for the enhancement of image quality of a tomographic image in an eye portion.

BACKGROUND ART

A tomographic imaging apparatus for the eye portion such as an optical coherence tomography (hereinafter referred to as OCT) is usable to three-dimensionally observe a state inside a retinal layer. In recent years, the tomographic imaging apparatus has attracted attention because it is useful in accurately diagnosing disease.

In an ophthalmologic diagnosis, there can be used a volume image for grasping the state of the entire retinal layer and a high image-quality two-dimensional tomographic image for grasping a layer which is not imaged on a low image-quality tomographic image. The volume image refers to aggregation of the two-dimensional tomographic images.

The image quality of the tomographic image acquired by the OCT depends on the strength of near infrared light incident on a retina. For this reason, the strength of the light with which the retina is irradiated needs to be increased to improve the image quality of the tomographic image. However, from the viewpoint of safety, the strength of the light with which the retina can be irradiated is limited. This requires the high image-quality tomographic image to be generated while the retina is being irradiated with near infrared light within the unquestionable strength of the light from the viewpoint of safety. To meet such a requirement, Japanese Patent Application Laid-Open No. 2008-237238 discusses a technique in which two-dimensional captured tomographic images are superposed on each other to generate a noiseless sectional image.

In Japanese Patent Application Laid-Open No. 2008-237238, however, a plurality of tomographic images are merely subjected to arithmetic mean. For this reason, in a case where correlation is low between the added tomographic images, a reduction in diagnosis information can be increased. In particular, since involuntary eye movement occurs in eyes, the entire areas of adjacent images are not always similar.

SUMMARY OF INVENTION

The present invention is directed to an improvement in quality of a tomographic image.

According to an aspect of the present invention, an image processing apparatus includes calculation means configured to calculate information indicating similarity among a plurality of tomographic images, and generation means configured to generate a tomographic image from the plurality of tomographic images based on the calculated information indicating similarity.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

FIG. 1 illustrates a configuration of an image processing system according to a first exemplary embodiment of the present invention.

FIG. 2A is a flow chart illustrating a tomographic image capturing process in an image processing apparatus according to the first exemplary embodiment.

FIG. 2B is a flow chart illustrating the tomographic image capturing process in the image processing apparatus according to the first exemplary embodiment.

DESCRIPTION OF EMBODIMENTS

Figure 3A:
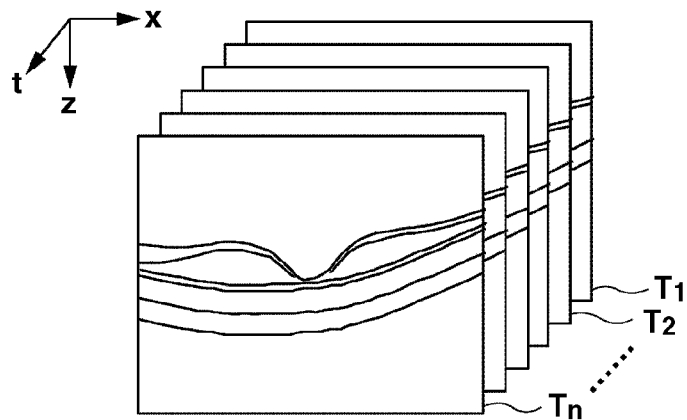
FIG. 3A is a diagram for describing superposition image generation processing.

Various exemplary embodiments, features, and aspects of the invention will be described in detail below with reference to the drawings.

FIG. 1 illustrates an image processing system 100 including an image processing apparatus 110 according to a first exemplary embodiment of the present invention. As illustrated in FIG. 1, the image processing system 100 is configured such that the image processing apparatus 110 is connected to a tomographic imaging apparatus 120 via an interface.

The tomographic imaging apparatus 120 is the one that captures a tomographic image of an eye portion and is comprised of a time-domain OCT or a Fourier-domain OCT, for example. The tomographic imaging apparatus 120 is a known apparatus, so that the detailed description thereof is omitted herein.

The image processing apparatus 110 includes an acquisition unit 111, a storage unit 112, an image processing unit 113, and a display control unit 114.

The acquisition unit 111 acquires a tomographic image captured by the tomographic imaging apparatus 120 and stores the captured tomographic image in the storage unit 112. The image processing unit 113 generates a new two-dimensional tomographic image from the tomographic images stored in the storage unit 112. The display control unit 114 performs control for displaying the processed image on a monitor (not illustrated).

A plurality of places may be sequentially scanned. As an example, however, FIG. 3A illustrates a schematic diagram of two-dimensional tomographic image groups in a macula lutea portion in which the tomographic imaging apparatus 120 continues repetitively scanning and imaging almost the same place. A direction in which scanning is performed with a measuring beam to capture a two-dimensional tomographic image is referred to as a main scanning direction. A direction orthogonal to the main scanning direction is referred to as a sub-scanning direction.

In general, the tomographic imaging apparatus 120 performs imaging in the main scanning direction while shifting the measuring beam in the sub-scanning direction. In other words, the present exemplary embodiment is also adaptable to a case where the measurement light is shifted in the sub-scanning direction.

In FIG. 3A, coordinate axes x and y and time base t are provided. FIG. 3A also illustrates two-dimensional tomographic images $T_1$ to Tn in the macula lutea portion imaged at different points of time. In other words, the two-dimensional tomographic image group is formed of aggregation of the two-dimensional tomographic images in which almost the same place is captured.

The enhancement of image quality refers to the improvement of S/N ratio. The improvement of image quality refers to the improvement of S/N ratio.

The processing by the image processing apparatus 110 according to the present exemplary embodiment is described below with reference to a flow chart in FIGS. 2A and 2B.

In step S201, a control unit (not illustrated) controls the tomographic imaging apparatus 120 to capture a retinal layer. A position in the direction of depth (a direction z in FIG. 3A) being a direction in which the retina is irradiated with the measuring beam and the direction of plane (a direction x in FIG. 3A) orthogonal to the direction z is adjusted. The alignment of position of direction of depth corresponds to the alignment of position of a coherent gate for acquiring a tomographic image.

In step S201, the control unit (not illustrated) performs adjustment to a position suitable for imaging the retinal layer. In step S202, an imaging instruction unit (not illustrated) issues instructions to start imaging.

In step S203, when an operator issues instructions for imaging, the control unit (not illustrated) repetitively scans almost the same place to capture a plurality of tomographic images.

The control unit (not illustrated) also has a function to adjust the distance of movement in the sub-scanning direction.

In step S204, the image processing unit 113 generates a new two-dimensional tomographic image using the two-dimensional tomographic image group stored in the storage unit 112. The generation of the two-dimensional tomographic image whose image quality is enhanced is described below with reference to FIG. 2B.

In step S210, a first alignment unit 115 aligns the two-dimensional tomographic images with one another. The alignment is performed such that an evaluation function indicating the similarity of two two-dimensional tomographic images, for example, is previously defined and the tomographic image is deformed so that the value of the evaluation function is maximized. A method for performing evaluation by a pixel value (a method for performing evaluation using the correlation coefficient of equation (1), for example), is used as the evaluation function. Processing in which translation or rotation is performed using affine transformation or magnification rate is changed is used as processing for deforming an image. The alignment may be performed on the basis of a feature point. A feature portion such as a retinal layer or a lesion is extracted from the two-dimensional tomographic image, for example. Since an internal limiting membrane, nerve fiber layer, visual cell inner-outer segment junction, and stratum pigmenti retinae are high in luminance and the boundary of the layer is high in contrast, the detection results on the layers and the feature portions are used to perform the alignment.

A deformation parameter is calculated at which the evaluation function is maximized while deforming the two-dimensional tomographic image to align the two-dimensional tomographic images with one another. If the number of two-dimensional tomographic images to be superposed is N, N−1 two-dimensional tomographic images are aligned with the two-dimensional tomographic image serving as a reference.

In step S211, a determination unit 117 determines A-scan images superposed in units of the corresponding A-scan images. This process is described below with reference to FIG. 4. Two-dimensional tomographic images Ti' and Ti+1' captured at different points of time are aligned in step S210. Aij' and A(i+1)j' represent the corresponding A-scan images in the aligned two-dimensional tomographic images Ti' and Ti+1'. The A-scan image in the present exemplary embodiment refers to one pixel row parallel to the direction of the z axis in FIG. 4.

The A-scan image is the one that agrees with the direction in which a measuring beam is incident. Each of the A-scan images acquired from the same place has almost the same image information. For this reason, even if the entire two-dimensional tomographic images are low in similarity due to involuntary eye movement, data mutually high in similarity can exist in the A-scan images of different two-dimensional tomographic images.

Image areas Rij' and R(i+i)j' each represent an area of +−.alpha. in the direction of the x axis with the A-scan images Aij' and A(i+1)j' as a center. A calculation unit 116 calculates a similarity between the A-scan images in the image areas Rij' and R(i+1)j' with the A-scan image as a center. In a case where a reference area for determining superposition is taken as the area Rij', the calculation unit 116 calculates a similarity between the areas corresponding to all of the areas Rij' to Rnj'. A formula using a correlation coefficient as an evaluation function indicating a similarity between the A-scan images is expressed by an expression (1).

[Math. 1]
[Math. 1]

$$\frac{\iint_S (f(x,y)-\overline{f})(g(x,y)-\overline{g})dxdy}{\sqrt{\iint_S (f(x,y)-\overline{f})^2 dxdy \iint_S (g(x,y)-\overline{g})^2 dxdy}} \quad (1)$$

Figure 4:
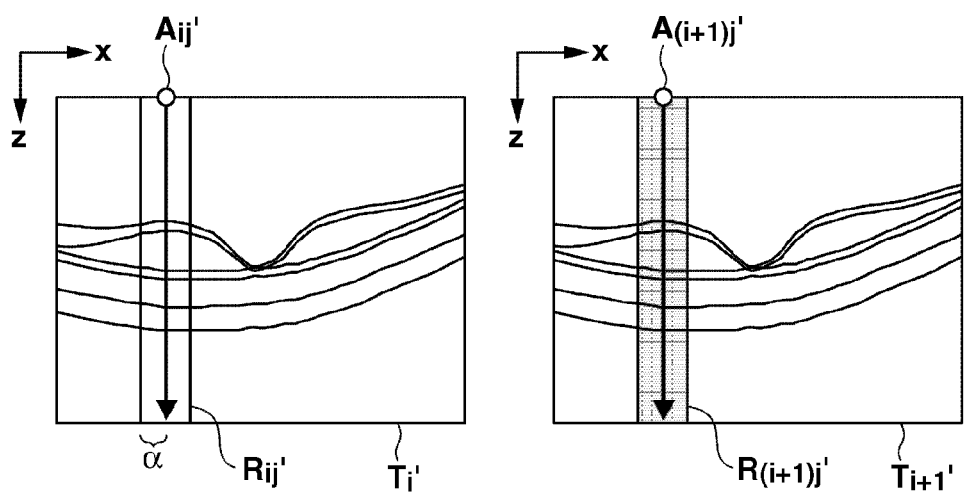
FIG. 4 is a diagram for describing superposition areas.

In FIG. 4, where the area Rij' is taken as f(x, y) and the area R(i+1)j' is taken as g(x, y), $\overline{f}$ and $\overline{g}$ [Math. 2]

represent the averages of areas f(x, y) and g(x, y), respectively.

Figure 5A:
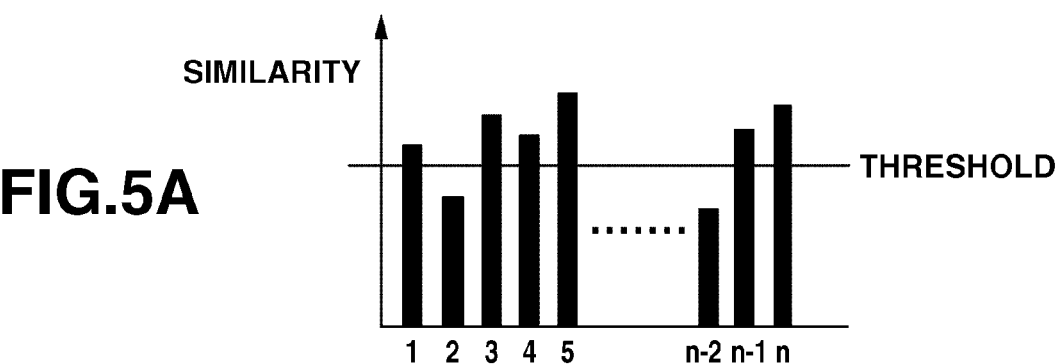
FIG. 5A is a diagram for describing superposition determination processing.
Figure 5B:
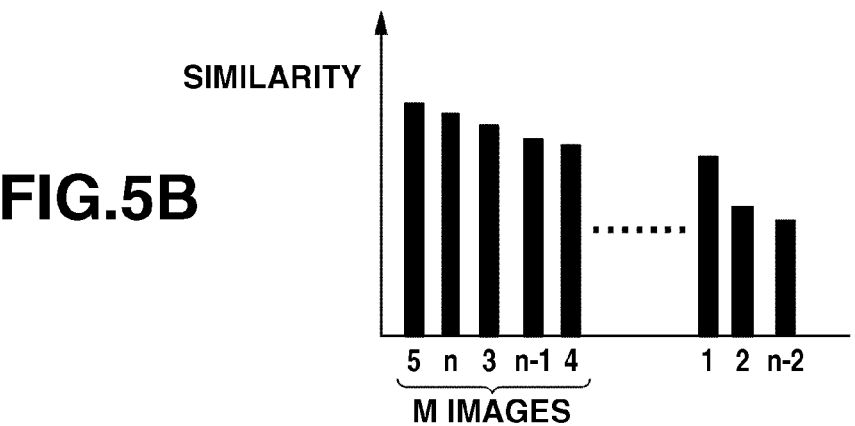
FIG. 5B is a diagram for describing the superposition determination processing.
Figure 5C:
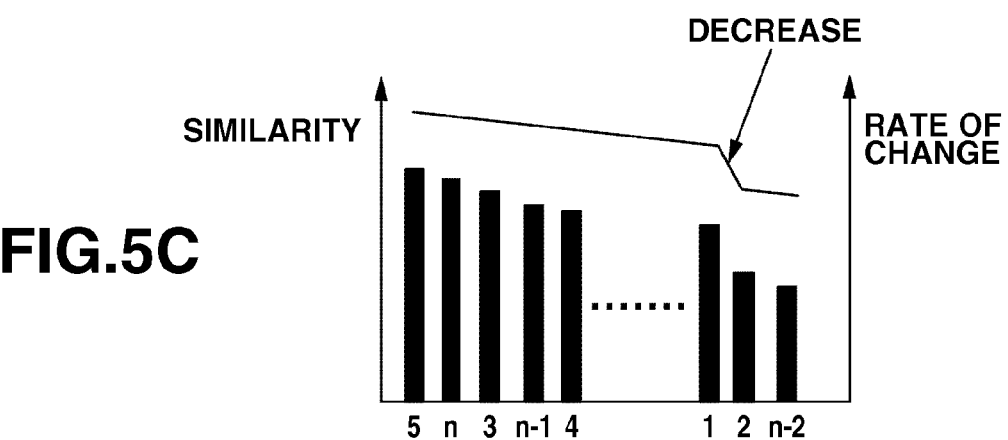
FIG. 5C is a diagram for describing the superposition determination processing.

The determination unit 117 selects an area used for superposition for each area. The processing by the determination unit 117 is described below with reference to FIGS. 5A to 5C. FIGS. 5A to 5C illustrate examples of results obtained by the calculation unit 116 calculating the similarity between areas.

The abscissa represents numbers 1 to N of the captured two-dimensional tomographic images. The ordinate signifies a similarity between a reference area and other areas in the two-dimensional tomographic images. FIG. 5A illustrates a method (a) for setting a threshold Th to select an area whose similarity exceeds a predetermined width value. FIG. 5B illustrates a method (b) for selecting top M images of similarity when the areas in FIG. 5A are sorted in descending order of similarity. FIG. 5C illustrates a method (c) for representing rates of change of similarity after the sorting process by a line graph when the areas in FIG. 5A are subjected to a sorting process in descending order of similarity. Here is illustrated an example where images are selected before the rate of change of similarity is significantly decreased. More specifically, the similarity at which the rate of change of similarity after the sorting process shows the predetermined width value is obtained to select the area whose value exceeds the obtained similarity.

In addition to the above, there is another method (d) for observing the rate of change of similarity without conducting the sort process. The calculation unit 116 stops calculating an evaluation value if the similarity is lower than a predetermined width value. An image in which the evaluation value is higher than the predetermined width value and the calculation thereof is still being performed is selected.

For the method (a) using the threshold, the area where the evaluation value is lower is not used for superposition, so that only the areas where the valuation value is high can be superposed.

This is suitable for the case where the movement distance per unit time in the sub-scanning direction is small. This is because the method has an effect in which an organization structure is changed a little but the image of the area which is greatly different in organization structure and is produced by unique movement or blinking of an eye is not selected.

For the method (b) selecting the fixed number M of images, the number of pieces of data subjected to superposition average processing in units of an image is not dispersed. The number of pieces of data subjected to superposition average processing in units of an A-scan image is also not dispersed. The extent that a noise is reduced can be leveled, so that the method (b) is suitable for the case where the image quality is equalized.

The method (c) using a rate of change is characterized in that the areas similar to each other can be selected even in the case where the image quality is inferior as a whole due to illness and the similarity is low as a whole.

The method (d) is suitable also for the case where the movement distance per unit time in the sub-scanning direction is large. This is because the calculation unit 116 can be prevented from unnecessarily calculating an evaluation value due to the reason that a displacement in the sub-scanning direction exceeding the predetermined width value makes the organization structure of retina different. In other words, a change in the organization structure can also be recognized by observing the rate of change.

As described above, the area where superposition is performed based on the evaluation value is selected in each area. For this reason, in the case where the retinal layer is deformed due to the involuntary eye movement in the two-dimensional tomographic image or in an area where the image quality is partially lowered due to blink or shading is not used for superposition, the image quality of a newly generated image is enhanced.

The determination unit 117 performs processing of combining the above methods (a) to (d) according to the movement distance per unit time in the sub-scanning direction. For example, in the case where the movement distance is shorter than a predetermined width value, the processing of the method (a) or (b) is used. In the case where the movement distance exceeds the predetermined width value, the processing of the method (c) or (d) is used. A combination of the methods (a) and (d) can perform the processing attaching importance to speed. A combination of the methods (b) and (d) can perform the processing attaching importance to image quality.

Figure 3B:
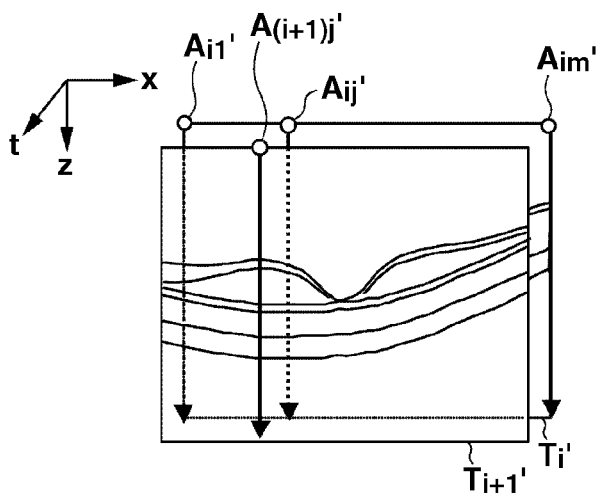
FIG. 3B is a diagram for describing the superposition image generation processing.
Figure 3C:
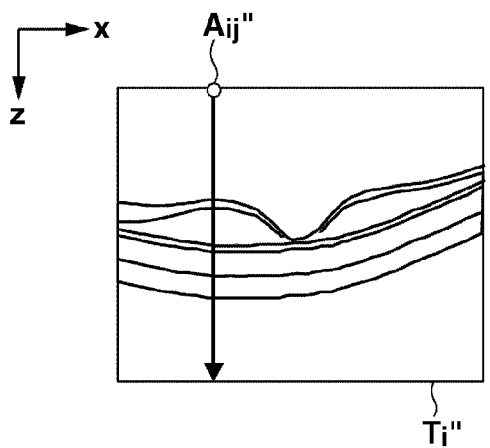
FIG. 3C is a diagram for describing the superposition image generation processing.

In step S212, a generation unit 118 performs superposition processing. The superposition of two A-scan images is described below. FIG. 3B is a diagram illustrating processing in which the two-dimensional tomographic images are processed in units of the A-scan image to generate one two-dimensional tomographic image as a composite image. In other words, an addition average processing of the A-scan images positioned on different two-dimensional tomographic images captured at different points of time is described as an example. FIG. 3C illustrates a high-quality two-dimensional tomographic image generated by performing the addition average processing using M pixels (two pixels in the example) for each pixel. In FIG. 3C, Aij" is a new A-scan image calculated by performing the addition average processing of the corresponding A-scan images.

In FIG. 3B, Ti' and Ti+1' represent two-dimensional tomographic images in which the same cross section is captured at different points of time. Aij' and A(i+1)j' represent A-scan images in the respective tomographic images Ti' and Ti+1'. The generation unit 118 performs the addition average processing of the A-scan images Aij' and A(i+1)j' to calculate the A-scan image Aij" in FIG. 3C. The generation processing of a high-quality two-dimensional tomographic image (composite image) is not limited to the addition average processing. A medium value calculation processing or a weighted addition average processing may be used. All of the A-scan images (Ai1' to Aim') of the reference image Ti' are subjected to these processing. In the weighted addition average processing, for example, the aforementioned similarity is used as weight of addition.

Although the present exemplary embodiment describes the case where an area where a similarity is calculated is taken as Rij' and the superposition processing is performed on Aij' (in units of the A-scan image), the present invention is not limited to the above exemplary embodiment. The superposition processing may be performed in units of the area where a similarity is calculated, for example. Alternatively, the superposition processing may be performed on two-dimensional tomographic images. Furthermore, the superposition processing may be performed such that a similarity is calculated in units of the A-scan image with .alpha. as 0 (Rij'=Aij' at .alpha.=0).

In step S205, the display control unit 114 displays the high-quality two-dimensional tomographic image generated in step S204 on a display unit (not illustrated). Although the above example describes that almost the same retinal area is scanned with the area fixed where the measuring beam of the tomographic imaging apparatus 120 is used for scanning, as described above, the present invention is applicable even if the entire retina is sequentially scanned.

As is understood from the above description, in the present exemplary embodiment, a similarity between the areas in a plurality of the aligned two-dimensional tomographic images is calculated using the corresponding A-scan images and a peripheral area and the area used for the superposition processing is determined in units of area. This allows a high-quality two-dimensional tomographic image to be generated because the area used for the superposition processing is determined in units of a partial area even in the case where the entire images are aligned but the retinal layer in the two-dimensional tomographic image is deformed due to involuntary eye movement.

According to the present exemplary embodiment, a high-quality two-dimensional tomographic image can be acquired even in the case where the two-dimensional tomographic image is deformed due to involuntary eye movement. The high-quality image refers to an image whose S/N ratio is made better than an image captured once. Alternatively, the high-quality image refers to an image in which the amount of information required for diagnosis is increased.

In the first exemplary embodiment, a similarity between the areas in the aligned two-dimensional tomographic images is calculated using the corresponding A-scan images and a peripheral area and the area used for the superposition processing is determined in units of area. In a second exemplary embodiment of the present invention, an area where the evaluation value is high in a neighbor area is searched in the aligned two-dimensional tomographic images using the A-scan images and a peripheral area to perform the superposition processing. According to the second exemplary embodiment, a general alignment is performed using a general characteristic, and alignment is performed using a local characteristic. Thereafter, the superposition processing is performed.

Figure 6:
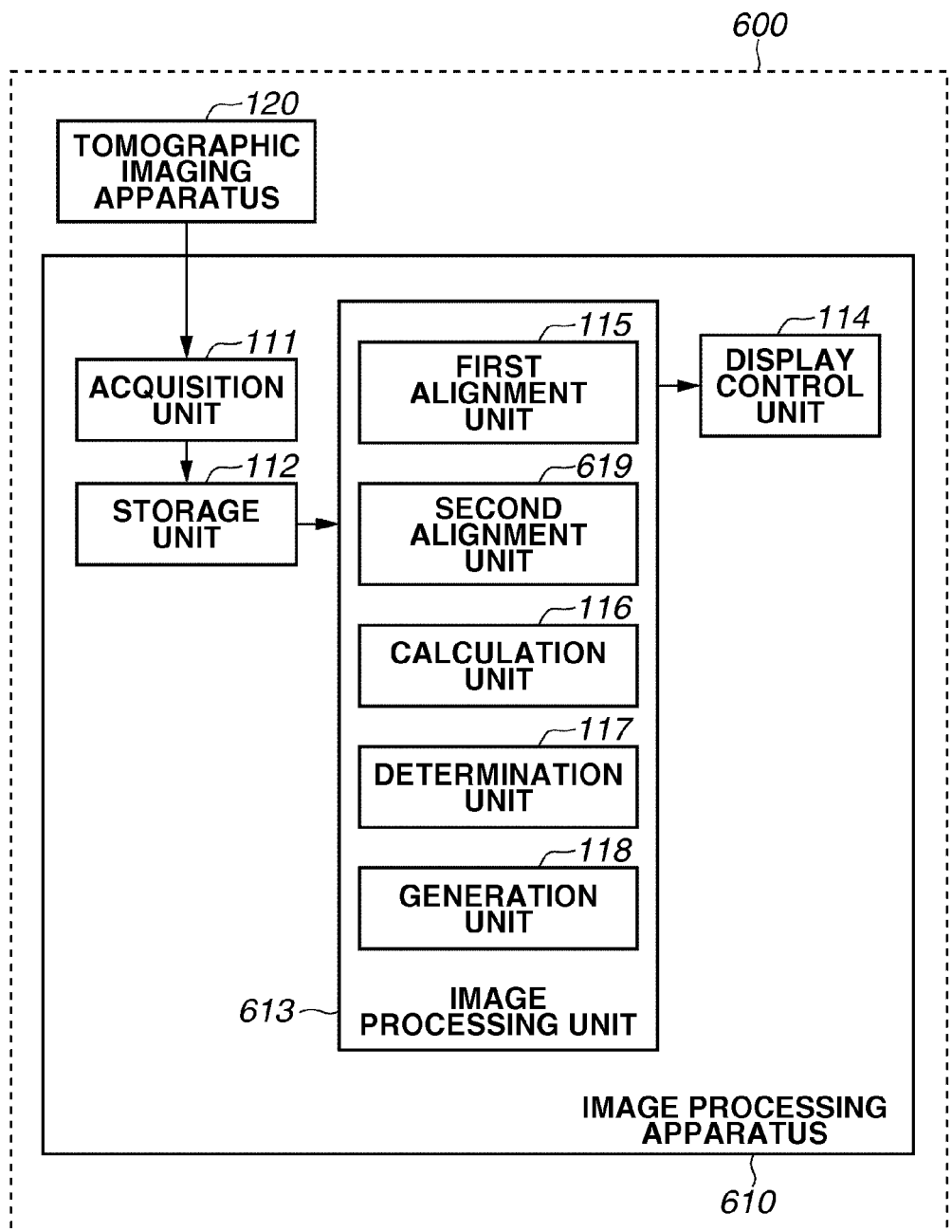
FIG. 6 is a block diagram illustrating a configuration of an image processing system according to a second exemplary embodiment of the present invention.
Figure 7A:
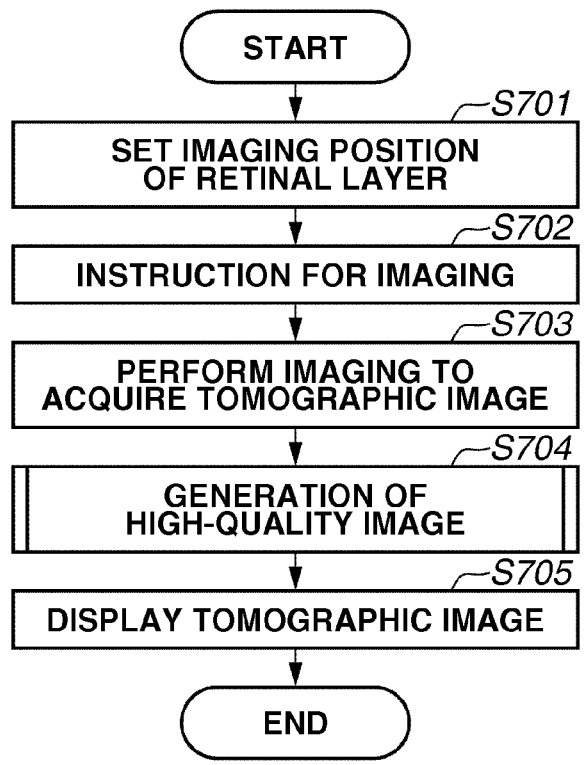
FIG. 7A is a flow chart illustrating a tomographic image capturing process in an image processing apparatus according to the second exemplary embodiment.
Figure 7B:
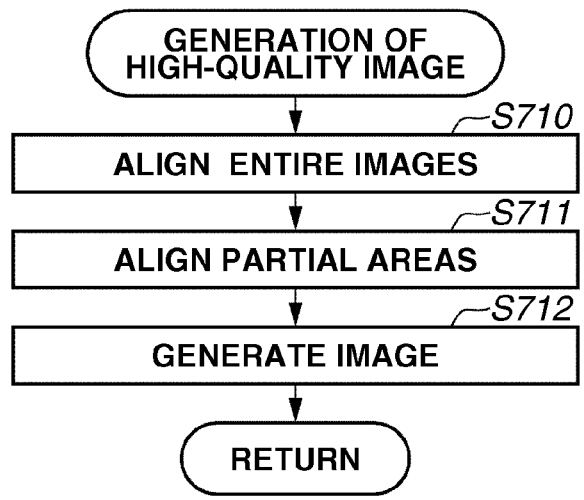
FIG. 7B is a flow chart illustrating the tomographic image capturing process in the image processing apparatus according to the second exemplary embodiment.

FIG. 6 is a block diagram illustrating a configuration of an image processing system 600 including an image processing apparatus 610 according to the second exemplary embodiment. As illustrated in FIG. 6, the image processing apparatus 610 includes the acquisition unit 111, the storage unit 112, an image processing unit 613, and the display control unit 114. The units excluding the image processing unit 613 have functions similar to those in the first exemplary embodiment, so that the description thereof is omitted herein.

In the image processing unit 613, a second alignment unit 619 performs a local alignment using the A-scan images and a peripheral area.

The processing by the image processing apparatus 610 according to the present exemplary embodiment is described below with reference to FIGS. 7A and 7B and FIGS. 8A to 8C. The steps other than step S704 are similar to steps S201 to S203 and step S205 in the first exemplary embodiment, so that the description thereof is omitted herein.

In step S704, the image processing unit 613 performs a general alignment and a local alignment to perform image superposition processing, thus generating a high-quality two-dimensional tomographic image. The generation processing of the high-quality two-dimensional tomographic image is described below with reference to FIG. 7B.

In step S710, the first alignment unit 115 aligns two-dimensional tomographic images with each other. The processing is similar to step S210 of the first exemplary embodiment, so that the description thereof is omitted herein.

In step S711, the two-dimensional tomographic images generally aligned in step S710 are aligned in units of the corresponding A-scan image to perform a local alignment. The processing is described below with reference to FIG. 8A. Ti' and Ti+1' represent images in which the same cross section is captured at different points of time, which are the two-dimensional tomographic images aligned in step S701. Aij' represents an A-scan image in the two-dimensional tomographic image Ti'. The shaded area Rij'' represents a range of +−.alpga. in the direction of the x axis with the A-scan image Aij' as a center. R(i+1)j'' represents a rectangular area corresponding to the range Rij'' in the two-dimensional tomographic image Ti+1'. S(i+1)j'' represents a search range for moving the rectangular area R(i+1)j''. If the reference A-scan image is taken as Aij' and an area where a similarity is calculated is taken as Rij'', the rectangular area R(i+1)j'' in the search range S(i+1)j' is scanned, and the calculation unit 116 calculates an evaluation value.

Figure 8A:
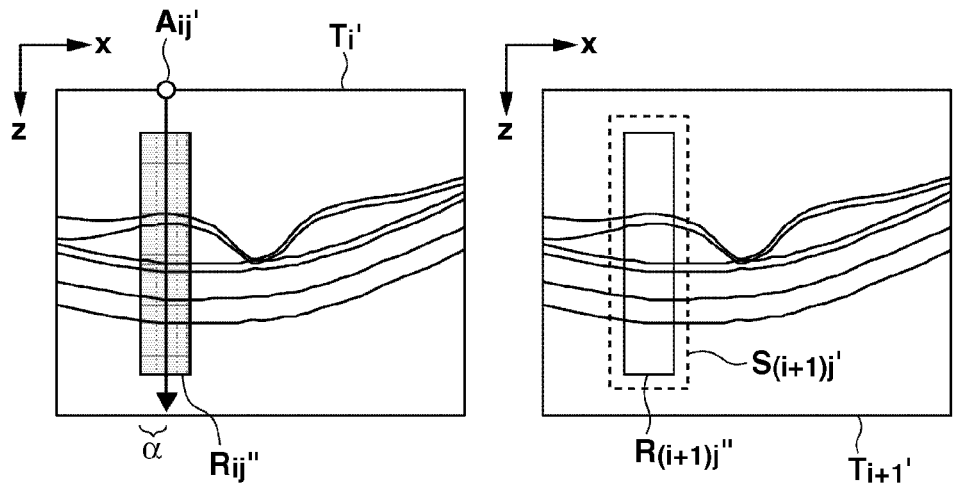
FIG. 8A is a diagram for describing superposition areas.
Figure 8B:
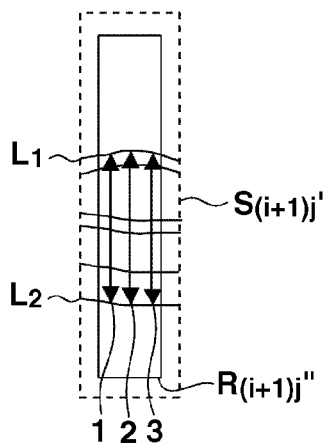
FIG. 8B is a diagram for describing the superposition areas.

The calculation unit 116 calculates the correlation of pixel values between the areas Rij'' and R(i+1)j'', and the determination unit 117 evaluates the evaluation value. Alternatively, the boundary of a retinal layer is detected to detect the thickness of the layer. The calculation unit 116 calculates the evaluation value of similarity using the thickness of the layer. FIG. 8B illustrates how the similarity is evaluated using the thickness of the layer. FIG. 8B illustrates the boundary of a retinal layer (an internal limiting membrane L1 and a stratum pigmenti retinae L2) in the search range S(i+1)j'' and the thickness values 1 to 3 of the layer. The thickness of the layer on each A-scan image is acquired in the rectangular area R(i+1)j''. The calculation unit 116 compares the thickness of the layers in the areas Rij'' and R(i+1)j'' with each other to calculate the evaluation value. The layer used for calculating the thickness of the layer is not limited to the above-mentioned layer. Other boundaries of a layer such as a nerve fiber layer or a visual cell inner-outer segment junction may be used to compare the thickness of the layer.

Although the superposition determination processing performed by the determination unit 117 is omitted in the present exemplary embodiment, it may be determined whether superposition is performed based on similarity after alignment is performed in units of the A-scan image as is the case with the first exemplary embodiment.

In step S712, the generation unit 118 performs processing for superposing the corresponding A-scan images with each other. More specifically, the generation unit 118 performs superposition processing between the A-scan image positioned at the center of the rectangular area R(i+1)j'' where the evaluation value is maximized and the reference A-scan image Aij'.

Figure 8C:
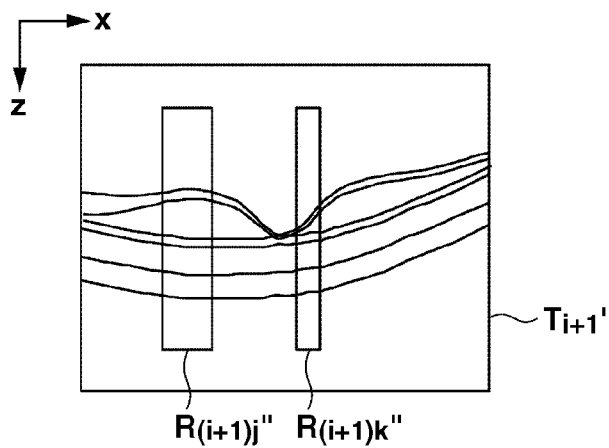
FIG. 8C is a diagram for describing the superposition areas.

In the present exemplary embodiment, the area Rij" is set as a rectangular area of the range of +−.alpha. with the position of the A-scan image as a center. As a method for setting the araa Rij", .alpha. may not be fixed, but may be dynamically changed according to an image feature of the retinal layer captured in the two-dimensional tomographic image. FIG. 8C illustrates an example of setting the area. For example, in a case where the retinal layer is planar, the range of .alpha. is set wide (R(i+1)j"). In a case where the retinal layer is curved and a characteristic place exists in the two-dimensional tomographic image (a large number of vertical and horizontal edges exist), the range of .alpha. is set narrow (R(i+1)k"). The range of an area may be changed for each case according to the image feature or may be changed in units of the A-scan image in one two-dimensional tomographic image.

As is apparent from the above description, in the present exemplary embodiment, an area where an evaluation value is high in a neighbor area is searched in the aligned two-dimensional tomographic images using the A-scan images and a peripheral area to perform the superposition processing. This allows a high-quality two-dimensional tomographic image to be generated because the local alignment is performed even in the case where the entire images are aligned but the retinal layer in the two-dimensional tomographic image is deformed due to involuntary eye movement.

The foregoing exemplary embodiments realize the present invention as an image processing apparatus. The exemplary embodiments of the present invention, however, are not limited only to the image processing apparatus. The present invention can be realized as software operating on a computer. A central processing unit (CPU) of the image processing apparatus controls the entire computer using computer programs and data stored in a RAM and a ROM. The CPU also controls the execution of software programs corresponding to the units of the image processing apparatus to realize the functions of the units.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

The invention claimed is:

1. An image processing apparatus comprising:
one or more processors; and
at least one memory storing instructions which, when executed by the one or more processors, cause the one or more processors to control:
a calculation unit to calculate similarity among partial areas each of which is a partial area of each of a plurality of tomographic images of a subject's eye obtained based on measurement light of an optical coherence tomography (OCT) controlled to scan a single position for a plurality of times, each of the partial areas having a predetermined width in a direction orthogonal to an A-scan direction in each of the plurality of tomographic images;
a selection unit to select a plurality of tomographic images corresponding to the partial areas the calculated similarity of which is higher than a predetermined value; and
a generation unit to generate an addition average image by adding and averaging the selected plurality of tomographic images for enhancement of image quality of a tomographic image in an eye portion of the subject's eye.

2. The image processing apparatus according to claim 1, wherein the calculation unit calculates similarity among the partial area of a reference tomographic image and the partial area of a different tomographic image as the similarity among the partial areas.

3. The image processing apparatus according to claim 1, wherein the one or more processors further causes an alignment unit to align the plurality of tomographic images,
wherein the similarity among the partial areas is similarity in a state where the plurality of tomographic images is aligned by the alignment unit.

4. The image processing apparatus according to claim 3, wherein the one or more processors further causes a layer detection unit to detect a layer from each of the plurality of tomographic images,
wherein the alignment unit aligns the plurality of tomographic images based on the layer detected by the layer detection unit.

5. The image processing apparatus according to claim 4, wherein the layer detected by the layer detection unit is any one of an internal limiting membrane, a nerve fiber layer, a visual cell inner-outer segment junction, and a stratum pigmenti retina.

6. The image processing apparatus according to claim 3, wherein the alignment unit performs the alignment based on similarity among the plurality of tomographic images, and
wherein a calculation method for the similarity among the partial areas is identical to a calculation method for the similarity among the plurality of tomographic images used by the alignment unit.

7. The image processing apparatus according to claim 1, wherein the OCT is a Fourier-domain OCT.

8. The image processing apparatus according to claim 1, wherein the tomographic image in an eye portion is a tomographic image of the fundus of the subject's eye.

9. A method for controlling an image processing apparatus, the apparatus including one or more processors and at least one memory storing instructions that, when executed by the one or more processors, cause the one or more processors to execute a method comprising:
calculating similarity among partial areas each of which is a partial area of each of a plurality of tomographic images of a subject's eye obtained based on measurement light of an optical coherence tomography (OCT) controlled to scan a single position for a plurality of times, each of the partial areas having a predetermined width in a direction orthogonal to an A-scan direction in each of the plurality of tomographic images;
selecting a plurality of tomographic images corresponding to the partial areas the calculated similarity of which is higher than a predetermined value; and
generating an addition average image by adding and averaging the selected plurality of tomographic images for enhancement of image quality of a tomographic image in an eye portion of the subject's eye.

10. The image processing method according to claim 9, wherein the calculating calculates similarity among the partial area of a reference tomographic image and the partial area of a different tomographic image as the similarity among the partial areas.

11. The image processing method according to claim 9, further comprising aligning the plurality of tomographic images, wherein the similarity among the partial areas is similarity in a state where the plurality of tomographic images is aligned in the aligning.

12. The image processing method according to claim 11, further comprising detecting a layer from each of the plurality of tomographic images,
wherein the aligning aligns the plurality of tomographic images based on the layer detected by the detecting.

13. The image processing method according to claim 12, wherein the layer detected by the detecting is any one of an internal limiting membrane, a nerve fiber layer, a visual cell inner-outer segment junction, and a stratum pigmenti retina.

14. The image processing method according to claim 11,
wherein the aligning performs the alignment based on similarity among the plurality of tomographic images, and
wherein a calculation method for the similarity among the partial areas is identical to a calculation method for the similarity among the plurality of tomographic images used by the aligning.

15. The image processing method according to claim 9, wherein the OCT is a Fourier-domain OCT.

16. The image processing method according to claim 9, wherein the tomographic image in an eye portion is a tomographic image of the fundus of the subject's eye.

17. A non-transitory storage medium storing a program for causing a computer to execute the image processing method according to claim 9.

18. An image processing apparatus comprising:
one or more processors; and
at least one memory storing instructions which, when executed by the one or more processors, cause the one or more processors to control;
a calculation unit to calculate similarity among partial areas each of which is a partial area of each of a plurality of tomographic images of a subject's eye obtained based on measurement light of an optical coherence tomography (OCT) controlled to scan a single position for a plurality of times, each of the partial areas having a predetermined width in a direction orthogonal to an A-scan direction in each of the plurality of tomographic images;
a selection unit to select a plurality of tomographic images corresponding to the partial areas the calculated similarity of which is higher than a predetermined value; and
a generation unit to generate an additional image of the subject's eye based on the selected plurality of tomographic images, a tomographic image which is not selected by the selection unit being not used for generating the additional image.

19. An image processing system including at least one processor comprising:
a calculation unit configured to calculate a degree of similarity among a plurality of tomographic images acquired based on a measuring beam controlled so that a same position is scanned with the measuring beam a plurality of times;
a generation unit configured to generate an additional image based on a plurality of tomographic images having a calculated degree of similarity being larger than a predetermined value;
an acquisition unit configured to acquire the plurality of tomographic images, wherein the acquisition unit is a Fourier-domain optical coherence tomography apparatus; and an alignment unit configured to align the plurality of tomographic images with one another,
wherein the calculation unit is configured to calculate the degree of similarity among the plurality of tomographic images after the plurality of tomographic images is aligned by the alignment unit.

20. The image processing system according to claim 19,
wherein the calculation unit is configured to calculate a degree of similarity between a reference tomographic image and a tomographic image different from the reference tomographic image, and
further comprising a determination unit configured to determine a tomographic image to be used by the generation unit for generating a composite image from the plurality of tomographic images based on the calculated degree of similarity.

21. The image processing system according to claim 19, wherein the alignment unit is configured to align the plurality of tomographic images with one another based on boundaries between layers of the plurality of tomographic images.

22. The image processing system according to claim 19, wherein the plurality of tomographic images are tomographic images of a subject's eye.

23. The image processing system according to claim 22, wherein the tomographic images of the subject's eye are tomographic images of a fundus of the subject's eye.

24. The image processing system according to claim 19, wherein the generation unit is configured to generate the additional image without using tomographic images having a degree of similarity being smaller than the predetermined value.

25. An image processing apparatus comprising:
a calculation unit to calculate a degree of similarity among partial areas, each of which is a partial area of each of a plurality of tomographic images of a subject's eye obtained based on measurement light of an optical coherence tomography (OCT) controlled to scan a single position for a plurality of times, each of the partial areas having a predetermined width in a direction orthogonal to an A-scan direction in each of the plurality of tomographic images;
a selection unit to select an A-scan image from a plurality of A-scan images corresponding to the plurality of tomographic images, wherein the A-scan image is included in the partial area having the calculated degree of similarity higher than a predetermined value; and
a generation unit to generate an additional A-scan image selected from the plurality of A- scan images,
wherein the width of the partial area in the direction orthogonal to the A-scan direction is wider than a width of the A-scan image.

26. The image processing apparatus according to claim 25,
wherein the partial area is an area having the A-scan image in a center, and
the A-scan image included in the partial area is an A-scan image in the center of the partial area.

27. The image processing apparatus according to claim 25,
wherein the calculation unit calculates the degree of similarity at each of different positions in the direction orthogonal to the A-scan direction, and
the selection unit selects the A-scan image at each of the different positions in the direction orthogonal to the A-scan direction.

28. An image processing apparatus comprising:
a first alignment unit to align a plurality of tomographic images of a subject's eye based on a layer boundary included in each of the plurality of tomographic images, the plurality of tomographic images being obtained based on measurement light of an optical coherence tomography (OCT) controlled to scan a single position for a plurality of times;
a second alignment unit to align the plurality of tomographic images in a unit finer than a unit of alignment in the first alignment unit in a direction orthogonal to an A- scan direction of the plurality of tomographic images, wherein the second alignment unit compares partial areas, each of which is a partial area of each of the plurality of tomographic images, each of the partial areas having a predetermined width in a direction orthogonal to an A-scan direction in each of the plurality of tomographic images aligned by the first alignment unit,
a generation unit to generate an additional A-scan image selected from the plurality of A- scan images.

29. The image processing apparatus according to claim 28,
wherein the second alignment unit aligns the plurality of tomographic images based on correlation of the partial areas of the plurality of tomographic images.

30. The image processing apparatus according to claim 28, wherein a size of the partial area in the direction orthogonal to the A-scan direction is variable.

31. The image processing apparatus according to claim 28,
wherein the second alignment unit aligns in an A-scan image unit.

32. The image processing apparatus according to claim 31,
wherein the partial area is an area having a predetermined width with the A-scan image subject to alignment in a center.

* * * * *